United States Patent [19]

Boyd et al.

[11] Patent Number: 5,599,839
[45] Date of Patent: Feb. 4, 1997

[54] ANTIVIRAL COMPOSITION

[75] Inventors: Michael R. Boyd, Ijamsville, Md.; Paul A. Cox, Provo, Utah; Gordon M. Cragg, Bethesda, Md.; Peter M. Blumberg, Frederick, Md.; Nancy A. Sharkey, Rockville, Md.; Junichi Ishitoya, Bethesda, Md.; James B. McMahon, Frederick, Md.; John A. Beutler, Braddock Heights, Md.; Owen S. Weislow, Reston, Va.; John H. Cardellina, II, Walkersville, Md.; Krik R. Gustafson, Wheaton, Md.

[73] Assignees: The United States of America as represented by the Department of Health and Human Services, Washington, D.C.; Brigham Young University, Provo, Utah

[21] Appl. No.: 424,558

[22] Filed: Apr. 17, 1995

Related U.S. Application Data

[63] Continuation of Ser. No. 530,562, May 30, 1990.
[51] Int. Cl.$^6$ ..................................................... A61K 31/22
[52] U.S. Cl. ................................................ 514/546
[58] Field of Search ........................................ 514/546

[56] References Cited

U.S. PATENT DOCUMENTS 4,902,716  2/1990  Higa et al. .......................... 514/546

OTHER PUBLICATIONS

Chu et al., J. Med Chem. 1989, 32 612–617.

Cashmore et al., Tetrahedron Letters No. 20, pp. 1737–1738 (1976).

Boyd, in AIDS Etiology, Diagnosis, Treatment, and Prevention, 2nd Edition, J. B. Lippincott Co, N.Y., pp. 305–319, 1987.

International Search Report.

"The structure of prostratin: A toxic tetracyclic Di Terpene ester from pimelea prostrata", Tetrahedron letters, 20:1737–1738 (1976) entire reference.

*Primary Examiner*—Jerome D. Goldberg
*Attorney, Agent, or Firm*—Leydig, Voit & Mayer, Ltd.

[57] ABSTRACT

The present invention relates to an antiviral composition and to methods of treating patients with viral infections. The antiviral composition of the present invention comprises prostratin, a phorbol ester derivative, and a pharmaceutically acceptable carrier. The present composition while having antiviral activity does not have substantial tumor promoting activity and does not have other substantial adverse toxicological properties that would preclude its use in antiviral therapy.

6 Claims, 4 Drawing Sheets

ANTIVIRAL COMPOSITION

This is a continuation of copending application Ser. No. 07/530,562 filed on May 30, 1990.

BACKGROUND OF THE INVENTION 1. Field of the Invention

The present invention relates to an antiviral composition, in particular an anti-HIV composition and to methods of treating viral infections. 2. Background Information A nucleoside class of antiviral agents, a prototype of which is AZT, is widely used in the clinical treatment of acquired immune deficiency syndrome (AIDS). AZT was initially selected for clinical use based upon an in vitro antiviral assay.

While extremely useful in antiviral therapy, AZT is limited by toxicity and a therapeutic index insufficient to make it adequate for therapy. Accordingly, new classes of antiviral agents to be used alone or in combination with AZT and other agents are urgently needed for effective antiviral therapy.

In the search for new antiviral agents, an extensive screening program to identify potential anti-AIDS and anti-cancer compounds from natural sources has been initiated [Boyd M. R.: In *AIDS Etiology, Diagnosis, Treatment and Prevention*, (DeVita V. T. Jr, Hellman S, Rosenberg S. A., eds.) Philadelphia: Lippincott, 1988, pp. 305–317]. Ongoing natural product collection projects are focusing on unusual or underexplored plant, marine and microbial resources.

As a part of this search, *Homalanthus acuminatus*, a small endemic tree of the primary forests of Samoa, and an important component of Samoan ethnopharmacology has been studied. Interviews with "taulasea", or Samoan healers, indicated that various parts of the plant are used to treat physical ailments. For example, the leaves are used in water infusions to treat back pain and abdominal swelling, the roots to suppress diarrhea and the stem wood to treat yellow fever [Cox P. A.: *Samoan Ethnopharmacology*. In *Economic and Medicinal Plant Research*, Vol. 4: *Plants and Traditional Medicine*. (Wagner H., Farnsworth N., eds.) London: Academic Press, in press]. Furthermore, related species are used in New Guinea (*H. nervosus*) to treat boils and sores [Holdsworth D. M.: *Int. J. Crude Drug Res.* 27:95–100, (1989)] and in Indonesia (*H. nutans*) for gonorrhea [Perry L. M.: *Medicinal Plants of East and Southeast Asia*. Cambridge: MIT Press, 1980, p. 149]. Also, the leaves of *H. nutans* have been used to treat circumcision wounds in Samoa [Uhe G.: *Econ. Bot.* 28:1–30, (1979)].

In the present invention, extracts of *H. acuminatus* are used to exert inhibitory effects against the human immunodeficiency virus (HIV-1), the causative agent of the AIDS.

SUMMARY OF THE INVENTION

Accordingly, it is an object of the present invention to provide a potent antiviral agent with minimal adverse toxicological properties.

It is another object of the present invention to provide an antiviral chemotherapeutic agent which has antiviral activity but does not have substantial tumor promoting activity.

In one embodiment, the present invention relates to an antiviral composition comprising an antivirally effective amount of prostratin and a pharmaceutically acceptable carrier.

In another embodiment, the present invention relates to a method of treating a viral infection comprising administering to a patient with the viral infection prostratin in an amount sufficient to effect said treatment.

Various other objects and advantages of the present invention will become apparent to one skilled in the art from the drawings and the following description of the invention.

DETAILED DESCRIPTION OF THE INVENTION

The present invention relates to an antiviral composition. The composition of the present invention comprises, as the active ingredient, the 12-deoxyphorbol ester derivative, prostratin and a pharmaceutically acceptable carrier. The prostratin of the present composition may be purified from a natural source or may be synthetically made. Suitable carriers for use in the present invention include, but are not limited to, injectable or orally or rectally administerable oils, lipid emulsions or aqueous suspensions, or in the case of orally or rectally administerable tablets or capsules, a pharmacologically inert excipient.

Utilizing an in vitro antiviral assay known to accurately predict antiviral activity in humans, prostratin was shown to have antiviral activity. In addition to its antiviral activity, prostratin substantially lacks tumor promoting activity, unlike most other phorbol esters. This lack of tumor-promoting activity makes prostratin extremely suitable for use as an antiviral agent and more desirable than other agents with anti-HIV activity which have tumor-promoting activity.

The compositions of the present invention inhibit the HIV retrovirus. As one skilled in the art will appreciate, prostratin and compositions thereof will likely inhibit other retroviruses and may inhibit non-retrovirus viruses.

Figure 2A:
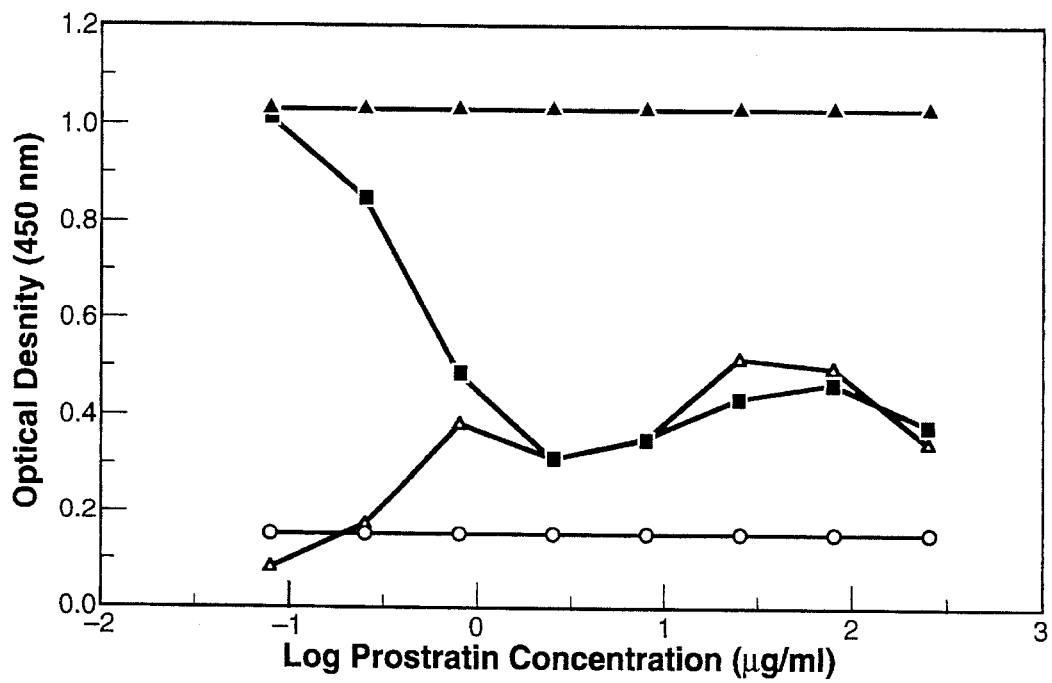
FIG. 2. Anti-HIV-1 activity of prostratin in CEM-SS cells. (A) Optical density readings in the XTT tetrazolium assay of untreated control cells (▲), prostratin-treated control cells (■), prostratin-treated cells infected with HIV-1 (Δ) and untreated cells infected with HIV-1 (○). (B) Reduction of viral p24 protein (□) and syncytium-forming units (●) following prostratin treatment.

The present invention further relates to a method of treating viral infections comprising administering to a patient an "effective amount", of the composition of the present invention. The "effective amount" is defined as that amount required to be administered to an individual patient to achieve an "effective blood level" of prostratin of ≧3µ molar (e.g. the approximate minimum level required for maximum antiviral activity—see FIG. 2). Since the fixed "effective blood level" is used as the prefered endpoint for dosing, the actual dose and schedule for drug administration for each patient may vary, depending upon interindividual differences in pharmacokinetics, drug disposition and metabolism. The composition can be administered, for example, orally, rectally, subcutaneously or intravenously. One skilled in the art can easily determine the appropriate method of administration for the exact formulation of the composition being used. The composition can be present in as a sterile solution suitable, for example, for intravenous administration. The composition can also be present in dosage unit form, such as, for example, as a tablet or capsule.

EXAMPLES

The following non-limiting Examples are provided to aid in the understanding of the present invention. It is understood that modifications can be made in the procedure set forth, without departing from the true spirit of the invention.
Ethnobotanical Techniques Interviews concerning the use of *Homalanthus acuminatus* (Muell.-Arg.) Pax were conducted in the Samoan language with healers in Falealupo and Pesega villages, Western Samoa. Bulk samples of stem wood and other parts of *H. acuminatus* were collected and shipped immediately to the NCI Natural Products Repository in Frederick, Md. U.S.A. Voucher specimens were collected at the same time, verified by healers, and subsequently deposited in the herbaria of Brigham Young University (BRG) and Harvard University (GH).

Isolation and Structure Determination

Large-scale separations, using high-performance liquid chromatography (HPLC), were performed initially with a Waters C-18 Prepak® 500 cartridge, and final purification was effected on a Rainin Dynamax® C-18 column (1×25 cm). $^1$H-NMR spectra were recorded on a Varian VXR 500 spectrometer and $^{13}$C-NMR spectra were recorded on a Varian XL 200 spectrometer. Chemical shifts are given in ppm relative to an internal standard of tetramethylsilane (TMS, δ=0). Infrared spectra were measured on a Perkin-Elmer 267 spectrometer and ultraviolet spectra were obtained with a Beckman 34 spectrophotometer. Optical rotations were measured on a Perkin-Elmer 241 polarimeter. Mass spectra were recorded on a VG Micromass ZAB 2F mass spectrometer.

Approximately 1.05 kg of fresh stem wood from *Homalanthus acuminatus* were extracted sequentially with ethanol and 1:1 dichloromethane-methanol to yield 22.8 g of extract. This crude extract was subjected to a modified Kupchan partition protocol [Grode et al.: *J. Org. Chem.* 48:5203–5207, (1983)]. The hexane-soluble and carbon tetrachloride-soluble fractions appeared rich in lipophilic phorbol esters, as determined by TLC and $^1$H-NMR analysis. The material that partitioned into chloroform (3.7 g) did not appear to contain long-chain alkyl esters of phorbol by $^1$H-NMR, but was active in the anti-HIV assay. The latter sample was further separated by gel permeation through Sephadex LH-20 (4×140 cm) with methanol/dichloromethane (1:1) into seven fractions. Fractions two and three were combined (2.3 g) and subjected to preparative HPLC using a water/methanol step gradient elution on C-18 reversed-phase sorbent. The fraction that eluted with 70:30 methanol/water (95 mg) was further purified by C-18 HPLC (70:30 methanol/water) to provide 15 mg of a pure compound which showed striking activity in the anti-HIV screen. Throughout the isolation procedure all fractions were tested for anti-HIV activity as described hereinbelow.

Figure 1:
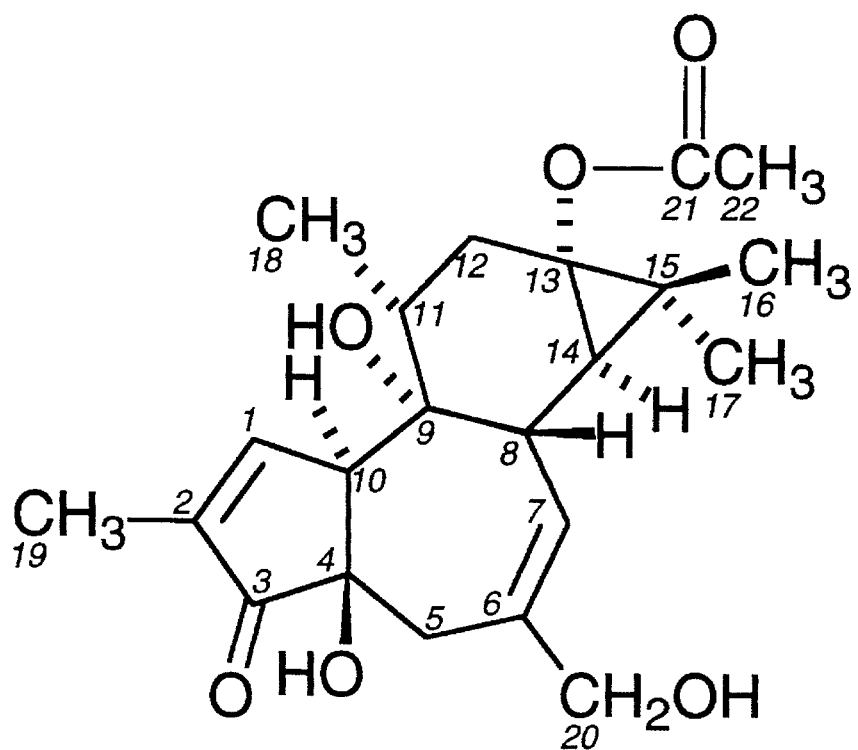
FIG. 1. Structure of the 12-deoxyphorbol ester prostratin.

The pure, active compound was an optically active, white crystalline solid, mp 215°–216°, $[\alpha]_D$+62.6° (c 0.9, MeOH). The molecular formula of $C_{22}H_{30}O_6$ was established by high-resolution, fast-atom bombardment (FAB) mass spectrometry (observed m/z 391.2088 for [MH$^+$], calculated m/z 391.2119 for $C_{22}H_{30}O_6$). These data, and precedents that many species of the family Euphorbiaceae produce phorbol diterpenes, suggested that the compound was a monoacetylated phorbol diterpene derivative. Characteristic ultraviolet absorbances (EtOH) at 210 (ε=8900) and 236 nm (ε=5900) and infrared bands (CHCl$_3$) at 3300, 1725 and 1705 cm$^{-1}$ supported this conclusion. Homonuclear decoupling and COSY (correlation spectroscopy) [Bax et al.: *J. Magn. Reson.* 44:542– 561, (1981)] analyses of the $^1$H-NMR spectra (500 MHz, CDCl$_3$) revealed a 12-deoxyphorbol nucleus. The $^1$H and $^{13}$C NMR resonances (See Table 1 below) were found to match literature values for a compound known as prostratin [Cashmore et al.: *Tetrahedron Lett.* 20:1737–1738, (1976) and Evans F. J.: *Naturally Occurring Phorbol Esters* (Evans F. J. ed.) Boca Raton, Fla.: CRC Press, 1986, pp. 171–215] whose structure (FIG. 1) had previously been established by X-ray crystallographic analysis [McCormick et al.: *Tetrahedron Lett.* 20:1735–1736, (1976).]

TABLE 1

NMR DATA FOR PROSTRATIN

| Carbon # | $^{13}$C$^a$ | $^1$H$^b$ |
|---|---|---|
| 1 | 161.2 | 7.50 (br s) |
| 2 | 140.0 | |
| 3 | 209.2 | |
| 4 | 73.8 | |
| 5 | 38.6 | 2.53 (2H, br s) |
| 6 | 132.8 | |
| 7 | 130.2 | 5.73 (d, J = 5.7) |
| 8 | 39.1 | 3.18 (dd, J = 5.7, 5.3) |
| 9 | 76.1 | |
| 10 | 55.1 | 3.48 (br s) |
| 11 | 32.4 | 2.13 (ddq, J = 11.6, 7.0, 6.4) |
| 12 | 31.8 | 1.70 (dd, J = 14.5, 11.6) |
|   |   | 2.01 (dd, J = 14.5, 7.0) |
| 13 | 63.6 | |
| 14 | 36.2 | 0.88 (d, J = 5.3) |
| 15 | 22.7 | |
| 16 | 23.2$^c$ | 1.09 (3H, s)$^d$ |
| 17 | 18.6$^c$ | 1.02 (3H, s)$^d$ |
| 18 | 15.3 | 0.98 (3H, d, J = 6.4) |
| 19 | 10.1 | 1.58 (3H, dd, J = 2.7, 1.3)$^e$ |
| 20 | 68.3 | 3.79 (dd, J = 12.7, 3.6) |
|   |   | 3.86 (br d, J = 12.7) |
| 21 | 173.2 | |
| 22 | 21.3$^c$ | 1.55 (3H, s) |

$^a$Spectrum obtained at 50 MHz in CDCl$_3$. Assignments were based on literature values for 12-deoxyphorbols [Cashmore et al.: Tetrahedron Lett. 20:1737–1738 (1976) and Evans FJ: in Naturally Occuring Phorbol Esters (Evans FJ ed.) Boca Raton, FL: CRC Press, 1986, pp. 171–215].
$^b$Spectrum obtained at 500 MHz in C$_6$D$_6$. Coupling constants are reported in Hertz. Assignments were based on homonuclear decoupled and COSY analysis.
$^c$Assignments may be reversed.
$^d$Assignments may be reversed.
$^e$Long range allylic and homoallylic couplings.

Screening for Anti-HIV-1 Activity

The XTT-tetrazolium anti-HIV assay was performed on crude extracts, chromatographic fractions and pure compounds as previously described [Weislow et al.: *J. Nat. Cancer Inst.* 81:577–586, (1989) and Gustafson et al.: *J. Nat. Cancer Inst.* 81:1254–1258, (1989)] but with several modifications. The human T-lymphoblastic cell line CEM- SS [Nara et al.: *AIDS Res. Hum. Retroviruses* 3:283–302, (1987)] was used as the target cell line and virus infections were performed using the RF variant of HIV-1, (MOI=0.05). Concentrated pellets of CEM-SS cells were incubated with the free virus for 1 hour at 37° C. The cells were then diluted and inoculated into round-bottomed 96-well microtiter plates (Corning) at a density of 5000 cells/well. Test compounds and the appropriate controls were then added to the wells, and the plates were incubated for 6 days. At the end of the incubation period cell growth parameters and HIV-1 activities were determined.

The relative numbers of viable cells in the cultures incubated with various concentrations of prostratin were estimated using the XTT-tetrazolium procedure; surviving cells metabolically reduce XTT to a colored formazan product which is measured colormetrically [Boyd M. R.: In *AIDS Etiology, Diagnosis, Treatment and Prevention*, (DeVita V. T. Jr, Hellman S., Rosenberg S. A., eds). Philadelphia: Lippincott, 1988, pp. 305–317; Weislow et al.: *J. Nat. Cancer Inst.* 81:577–586, (1989) and Gustafson et al.: *J. Nat. Cancer Inst.* 81:1254–1258, (1989)].

An interesting result was obtained (FIG. 2A), which clearly showed the importance of inclusion of the uninfected, drug-treated controls for proper interpretation of the XTT assay results. Viewed in isolation, the XTT assay data on the virus-infected cells would have indicated only a modest enhancement in cellular production of XTT-formazan production in the presence of 1.0–200 µg/ml of prostratin. However, in comparing the effects of prostratin over the same concentration range on the uninfected cells, it was apparent that the agent had a marked growth-inhibitory, or cytostatic, effect on these control cultures. Therefore, what might have initially appeared to be only a modest antiviral effect of prostratin was actually quite profound. In the presence of a broad range of concentrations of prostratin the number of viable cells, as indicated by XTT-formazan production, was essentially identical in the uninfected cell cultures or in the cultures infected with HIV-1.

Figure 2B:
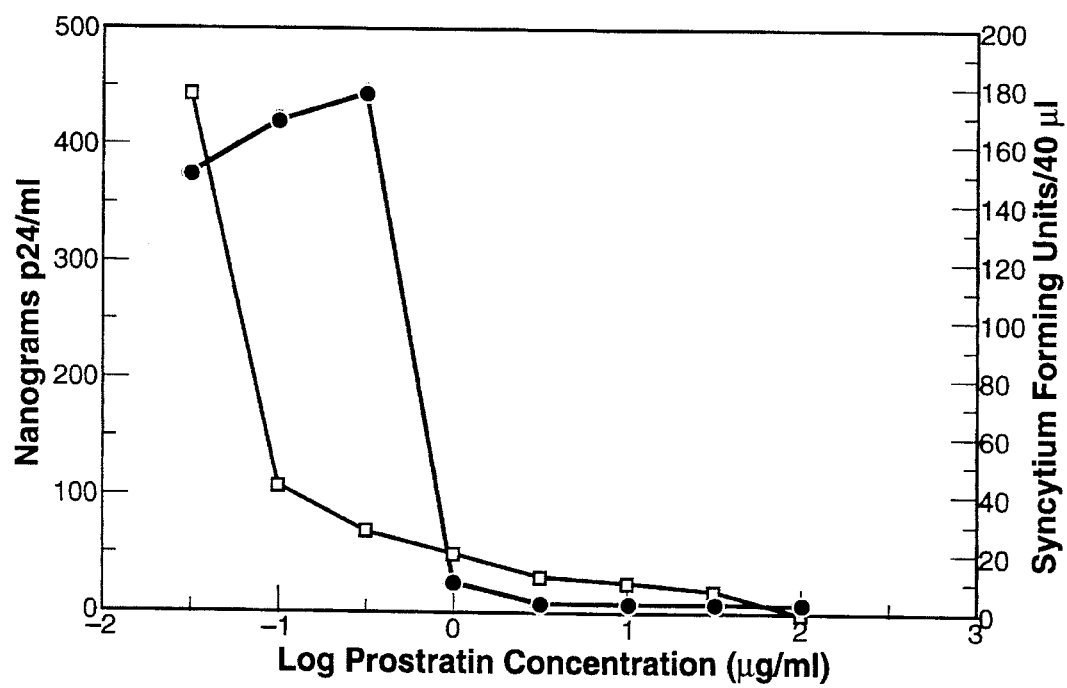

Aliquots of supernatant fluid from the test wells of the tetrazolium assay were removed prior to the time of XTT addition for quantitation of residual infectious virus using the syncytium assay described by Nara et al. [Nara et al.: *AIDS Res. Hum. Retroviruses* 3:283:302, (1987)]. Data were expressed as syncytium-forming units (SFU/40 µl). Other aliquots were diluted 1:100 with Triton X-100 and analyzed for the HIV core protein, p24, as previously described [Gustafson et al.: *J. Nat. Cancer Inst.* 81:1254–1258, (1989)]. Correlative assays measuring the effects of prostratin on p24 viral antigen production and syncytium formation as an estimate of infectious virions, shows similarly striking inhibitory effects of prostratin at concentrations as low as 1.0 µg/ml (FIG. 2B).

Trypan Blue Dye Exclusion Assay

Trypan blue dye exclusion was employed for secondary evaluation of drug toxicity and antiviral protection over time. A 50 µl aliquot of cells was removed from each test well and mixed with 100 µl of 0.4% trypan blue. The percentage of viable cells was determined microscopically by direct hemocytometer counts. The assays indicated that cell viability was greater than 90 percent for both the infected and uninfected cultures treated with prostratin (FIG. 4).

Figure 3:
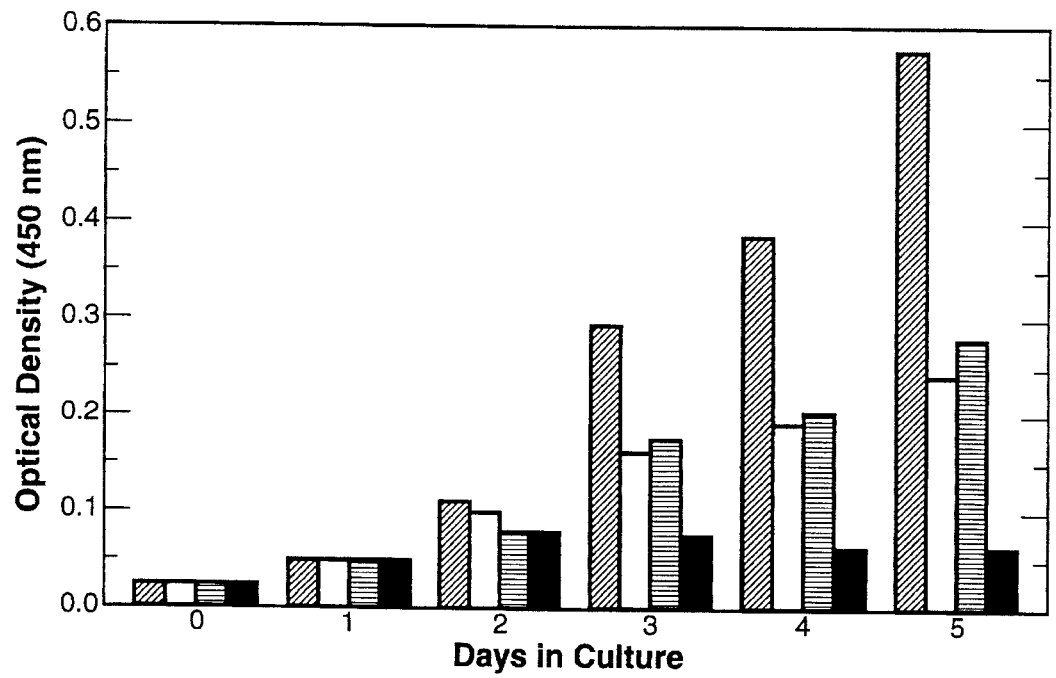
FIG. 3. XXT formazan production determined after 1–5 days in uninfected CEM-SS cells (⊠), prostratin (10 µg/ml)-treated CEM-SS cells (□), prostratin (10 µg/ml)-treated CEM-SS cells infected with HIV-1 (▫), and untreated CEM-SS cells infected with HIV-1 (■).
Figure 4:
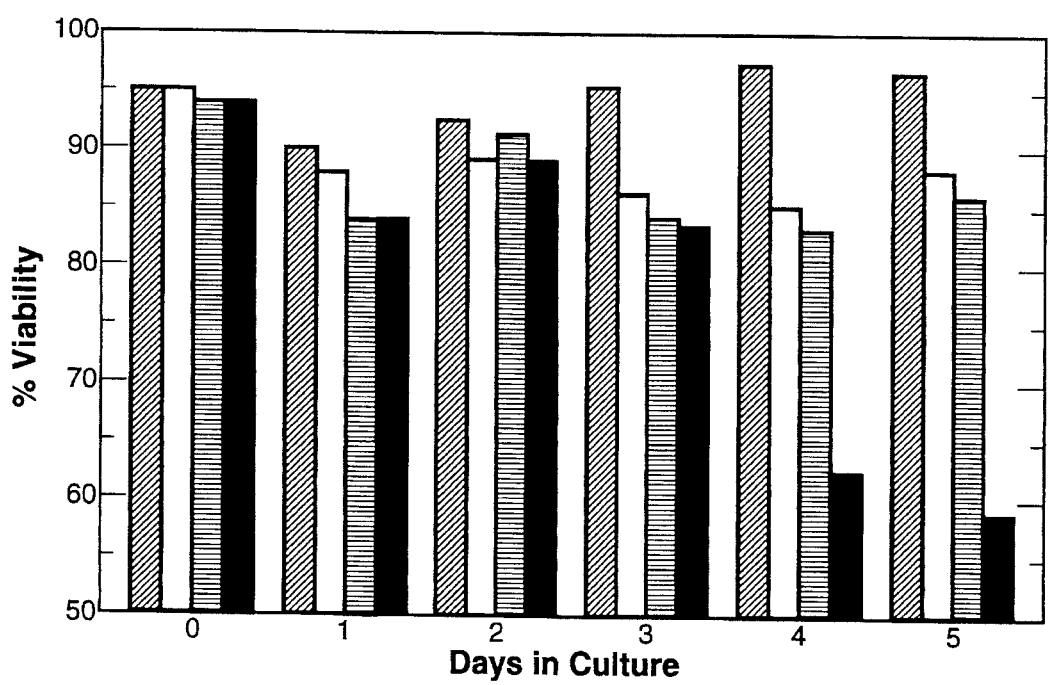
FIG. 4. Effect of prostratin on cell viability. Percentage of cell viability determined by trypan blue dye exclusion for control cells (⊠), prostratin treated control cells (□), prostratin treated cells infected with HIV-1 (▫) and untreated cells infected with HIV-1(■).
Figure 5A:
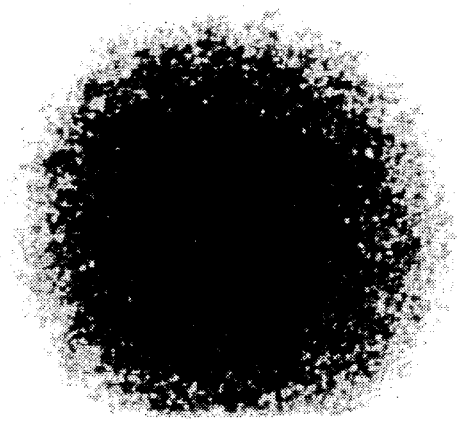
FIG. 5. Effect of prostratin (10 µg/ml) on CEM-SS cell colony morphology after 6 days in culture for control cells (A), prostratin-treated control cells (B) prostratin-treated cells infected with HIV-1 (C) and untreated cells infected with HIV-1 (D).
Figure 5B:
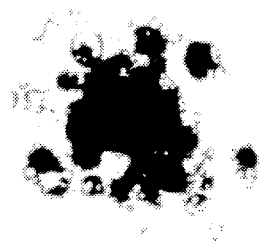
Figure 5C:
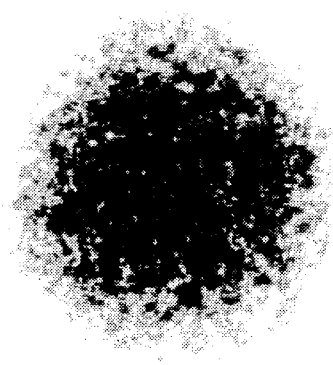
Figure 5D:
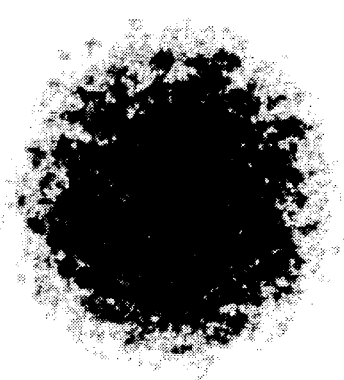

FIGS. 3 and 4 illustrate results of a series of experiments, each performed as described above, except that instead of using 6-day incubation, cell viability assays were performed after 0, 1, 2, 3, 4 and 5 days of incubation. The data shown in FIG. 3 were obtained using the XTT-tetrazolium assay, whereas the data in FIG. 4 are from a trypan blue dye exclusion assay. In both cases, the results are entirely consistent with the data and interpretations from FIG. 2, further confirm the cytostatic effect of prostratin on the CEM-SS target cells, and illustrate the impact of this effect on the assessment of the anti-HIV activity of prostratin. With either of the cell viability end-point assays, the anti-HIV activity of prostratin is strikingly apparent after three or more days of culture growth.

Protein Kinase C Assay

Binding of [$^3$H]phorbol 12,13-dibutyrate ([$^3$H]PDBu) to protein kinase C partially purified through the DEAE-chromatography step [Jeng et al.: *Cancer Res.* 46:1966–1971, (1986)] was assayed in the presence of phosphatidylserine as described [Sharkey et al.: *Cancer Res.* 45:19–24, (1985)] except that incubation was for 5 min at 37° C. Competition of [$^3$H]PDBu binding by prostratin was determined in the presence of 4 nM [$^3$H]PDBu. Binding of [$^3$H]PDBu to intact CEM-SS cells and competitive binding by prostratin were assayed in RPMI cell culture medium containing 0.1 mg/ml of bovine serum albumin, 25 mM Hepes, pH 7.4. Incubation was for 30 min at 37° C., after which the cells were chilled, an aliquot removed to determine total counts, and bound counts determined by filtration. Non-specific binding was determined in the presence of 5 µM non-radioactive PDBu. Activation of protein kinase C enzymatic activity by PDBu or prostratin was determined by the procedure of Nakadate et al. [Nakadate et al.: *Biochem. Pharmacol.* 37:1541–1545, (1988)]

Because prostratin is a phorbol derivative, it was of interest to see if it would bind to and activate, or inhibit, protein kinase C [Blumberg P. M.: *Cancer Res.* 48:1–8, (1988) and Nishizuka Y.: *Nature* 308:693–698, (1984)]. Interestingly, in contrast to many other phorbol derivatives, prostratin reportedly is not a tumor promoter [Zayed et. al.: *Experientia* 33:1554:1555, (1977)]. The $K_i$ for prostratin was 12.5±0.4 nM (mean±SEM; 3 experiments). For comparison, the $K_i$ value for 12-deoxyphorbol 13-isobutyrate was 2.1±0.1 nM (mean±range; 2 experiments) and the $K_d$ for PDBu was 0.59 nM. Prostratin, like PDBu, stimulated protein kinase C (PKC) activity in vitro; at a concentration of 1000 nM prostratin, stimulation of PKC was 95% of that exhibited by a concentration of 100 nM PDBu.

Binding affinities of phorbol esters in cells are typically lower than those obtained with reconstituted protein kinase C [Blumberg et al.: in *Mechanism of Tumor Promotion*, Vol. 3. *Tumor Promotion and Cocarcinogenesis in vitro*, (Slaga T. J., ed.) Boca Raton, Fla.: CRC Press, 1984, pp. 143–184], presumably reflecting the role of cellular calcium and phospholipid composition on binding [Konig et al.: *J. Cell. Biochem.* 7:255–265, (1985)]. In the CEM-SS cells, [$^3$H]PDBu was bound with an affinity of 4.9±0.8 nM (mean±range; 2 experiments) and a $B_{max}$ of 1.2±0.1 pmol/mg protein (mean±range; 2 experiments). Prostratin inhibited [$^3$H]PDBu binding to the CEM cells with a $K_i$ of 210±30 nM (mean±range; 2 experiments). The usual binding protocol were cells omits serum, because of reportedly variable effects of serum on binding [Blumberg et al.: in *Mechanism of Tumor Promotion, Vol. 3. Tumor Promotion and Cocarcinogenesis in vitro*, (Slaga T. J., ed.) Boca Raton, Fla.: CRC Press, 1984, pp. 143–184]. In any case, a substantial effect when 10% fetal calf serum was included in the assays of biological response was not observed in the CEM cells on the $K_i$ for prostratin ($K_i$=190 nM; one experiment).

Well-characterized biological responses to the phorbol esters include inhibition of binding of epidermal growth factor and release of arachidonic acid metabolites

[Dell'Aquila et al.: *Cancer Res.* 48:3702–3708, (1988)]. It was confirmed that prostratin induces both of these responses in C3H1OT1/2 cells.

C3H1OT1/2 cells were grown and [$^3$H] arachidonic acid metabolite release determined as described previously [Dell'Aquila et al.: *Cancer Res.* 48:3702–3708, (1988)]. $^{125}$I-epidermal growth factor binding by C3H10T1/2 cells was assayed as described [Dell'Aquila et al.: *Cancer Res.* 48:3702–3708, (1988)] using a 1 hr pretreatment with phorbol ester and then a 1 hr co-incubation with the phorbol ester and the $^{125}$I-epidermal growth factor.

The half-maximally effective concentrations of prostratin were 220 nM and 1100 nM, respectively. The corresponding values for PDBu, determined in parallel, were 10 and 24 nM, respectively.

Since prostratin acted like a typical phorbol ester in vitro, both in PKC enzyme preparations and in intact cells, albeit with 20–45-fold lower potency than PDBu, the activity of other phorbol derivatives in the anti-HIV assay was examined. The phorbol esters PMA (phorbol 12-myristate 13-acetate), at a concentration of 50 nM, and PDBu (500 nM) were similarly cytostatic and protective against HIV-1 under the above-described experimental conditions.

Cell Morphology

Low-power photomicrographs (FIG. 5) taken of CEM-SS cells after 6 days in culture under varying experimental conditions vividly revealed both the antiproliferative and the anti-HIV-1 effects of prostratin treatment.

Panel A illustrates uninfected control CEM-SS cells which have not been treated with prostratin. The cells form a uniform pellet several hundred cell diameters thick on the bottom surface of the rounded well. In this culture configuration the cells are in very close proximity to one another; however, they are not physically attached and can be separated by gentle agitation. Infection of CEM cells by HIV-1 results in dramatic morphological alterations after 6 days (panel B); the effects include giant cell (syncytia) formation, cell lysis and production of large quantities of cellular debris. In contrast, the macroscopic morphology of cell pellets of uninfected CEM cells (panel C) and cells infected with HIV-1 (panel D), both treated with 10 μg/ml prostratin, were virtually identical.

Prostratin treatment caused a decrease in the size of the cell pellet relative to the control cells in both cultures. However, the size of the cell pellet and the percentage of viable cells in cultures infected with HIV-1 and uninfected cultures were similar after prostratin treatment. Thus, although prostratin inhibited cell proliferation, it also appeared to block totally the cytopathic effects of HIV-1 infection.

Observations of cellular morphology at higher magnifications confirmed that, in the presence of 1 μM prostratin, syncytium formation was completely abolished.

All publications mentioned hereinabove are hereby incorporated by reference.

While the foregoing invention has been described in some detail for purposes of clarity and understanding, it will be appreciated by one skilled in the art from a reading of this disclosure that various changes in form and detail can be made without departing from the true scope of the invention.

We claim:

1. A method of treating a viral infection sensitive to treatment with prostratin in a patient comprising administering to said patient prostratin in an amount sufficient to effect said treatment.

2. The method of claim 1, wherein said prostratin is administered to said patient with a pharmaceutically acceptable carrier.

3. The method of claim 1, wherein said virus is a retrovirus.

4. The method of claim 3, wherein said prostratin is administered to said patient with a pharmaceutically acceptable carrier.

5. The method of claim 3, wherein said retrovirus is a human immunodeficiency virus.

6. The method of claim 5, wherein said prostratin is administered to said patient with a pharmaceutically acceptable carrier.

* * * * *